United States Patent [19]

Gomm et al.

[11] 4,088,673

[45] May 9, 1978

[54] PROCESS FOR THE PREPARATION OF STYRYL DYESTUFFS

[75] Inventors: Walter Gomm, Cologne; Hermann Beecken, Schildgen, both of Germany

[73] Assignee: Bayer Aktiengesellschaft, Leverkusen, Germany

[21] Appl. No.: 633,040

[22] Filed: Nov. 18, 1975

Related U.S. Application Data

[63] Continuation of Ser. No. 444,835 Feb. 22, 1974, abandoned.

[30] Foreign Application Priority Data

Feb. 22, 1973 Germany .............................. 2308706

[51] Int. Cl.$^2$ .................. C07C 121/78; C07D 215/16; C07D 277/80
[52] U.S. Cl. ............................... 260/465 E; 544/54; 542/427; 542/438; 542/439; 542/440; 260/281 N; 260/283 CN; 260/293.75; 260/294.8 G; 260/304 A; 260/304 R; 260/306.6 R; 260/306.7 R; 260/307 D; 260/325 R; 260/326 N; 260/326.5 FM; 260/326.5 FL; 260/329.5; 260/347.2; 260/463; 260/465 D
[58] Field of Search ........ 260/465 D, 465 E, 283 CN; 542/438, 427

[56] References Cited

U.S. PATENT DOCUMENTS

| | | | |
|---|---|---|---|
| 3,398,152 | 8/1968 | Wallace et al. ................. | 260/465 X |
| 3,917,604 | 11/1975 | Hoyle ............................. | 260/283 CN |

*Primary Examiner*—Dolph H. Torrence
*Attorney, Agent, or Firm*—Plumley & Tyner

[57] ABSTRACT

Process for the preparation of styryl dyestuffs, characterized in that, in a one-pot reaction, amines of the general formula

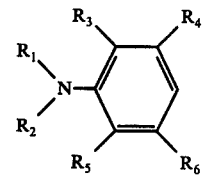

wherein
$R_1$ denotes alkyl or aryl,
$R_2$ denotes hydrogen, alkyl or aryl,
$R_3$–$R_6$ denote hydrogen or non-ionic substituents, preferably alkyl, alkoxy, nitro or halogen or $R_1$ with $R_3$ or $R_5$ conjointly from the remaining members of a 5-membered or 6-membered ring system which optionally contains further hetero-atoms are treated with at least 1 equivalent of a Vilsmeier reagent, unconverted Vilsmeier reagent is decomposed, the pH value is adjusted to above 4 by addition of bases and subsequently—without any intermediate isolation—the product is treated with a methylene-active compound of the formula

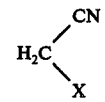

wherein
X represents a nitrile or acyl group.

6 Claims, No Drawings

PROCESS FOR THE PREPARATION OF STYRYL DYESTUFFS

This is a continuation of application Ser. No. 444,835, filed Feb. 22, 1974, now abandoned.

The present invention relates to a new process for the preparation of water-insoluble styryl dyestuffs which are free of ionogenic groups, of the general formula

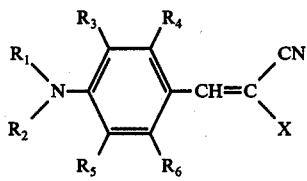

in which
- $R_1$ denotes alkyl or aryl,
- $R_2$ denotes hydrogen, alkyl or aryl,
- $R_3$–$R_6$ denote hydrogen or non-ionic substituents, preferably alkyl, alkoxy, nitro or halogen, or $R_1$ with $R_3$ or $R_5$ conjointly form the remaining members of a 5-membered or 6-membered ring system which optionally contains further hetero-atoms and
- X represents a nitrile or acyl group and the abovementioned alkyl, alkoxy, acyl and aryl radicals can contain further non-ionic substituents.

The styryl compounds of the indicated formula, which are known to be very valuable textile dyestuffs, were hitherto obtained exclusively by reacting aldehydes of the formula

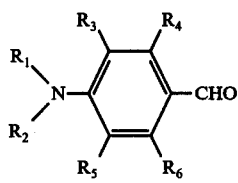

with methylene-active compounds of the formula

in the presence of basic catalysts, under the conditions of the Knoevenagel reaction.

However, this process method has the disadvantage that the aldehydes (II) to be used in it are as a rule compounds which are relatively difficult to obtain. In many cases, they are viscous oils or low-melting compounds which can in general only be purified by high vacuum distillation or by recrystallisation from organic solvents, with high losses in yield.

It has now been found that styryl dyestuffs can be prepared simply and in very good overall yields if, in a one-pot reaction, amines of the general formula

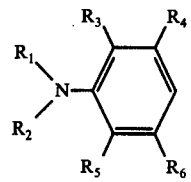

wherein
$R_1$–$R_6$ have the abovementioned meaning
are treated with at least 1 equivalent of a Vilsmeier reagent, unconverted Vilsmeier reagent is decomposed, the pH value is adjusted to above 4 by addition of bases and subsequently—without any intermediate isolation—the product is treated with a methylene-active compound of the formula

wherein
X has the abovementioned meaning.

The increases in yield achievable by the new process in comparison to the processes practiced hitherto are in general 20 to 50% based on the starting materials (III) and (IV).

By Vilsmeier reagents in the broadest sense there are to be understood compounds which transfer carbonyl groups, such as are obtained, in a known manner (see, for example, Houben-Weyl, "Methoden der organischen Chemie" ("Methods of Organic Chemistry"); volume VII/1, page 29 et seq) by treatment of carboxylic acid amides with special acid halides such as $POCl_3$, $SOCl_2$ and $COCl_2$.

In particular, compounds such as are defined in more detail by Bossard and Zollinger in Helv. chim. acta 42, 1659 (1959) and which correspond to the general formula

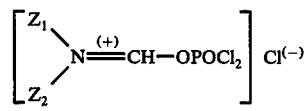

in which
- $Z_1$ denotes hydrogen, methyl or ethyl and
- $Z_2$ represents $Z_1$ or phenyl or
- $Z_1$ and $Z_2$ conjointly can form the remaining members of a piperidine or morpholine ring.

are to be regarded as Vilsmeier reagents.

Suitable carboxylic acid amides for the preparation of the reagent are: N-methylformamide, N-ethylformamide, di-N,N-butylformamide, N-methylformamide, N-benzyl-N-methylformamide, N-formylpiperidine, N-formylmorpholine and above all N,N-dimethylformamide. The use of a Vilsmeier reagent prepared from dimethylformamide and $POCl_3$ has proved particularly advantageous.

A possible reaction medium for the reaction according to the invention is, in particular, excess carboxylic acid amide, that is to say, for example, dimethylformamide.

The reaction temperatures can vary within a substantial range.

The reaction of the amine component IV with the Vilsmeier reagent is in general carried out at temperatures of 20° to 90° C, preferably of 50° to 70° C.

The decomposition of excess Vilsmeier reagent and the adjustment of the pH to the requisite value is carried out at temperatures of 10° to 80° C, preferably 30° to 60° C.

The last reaction step, the reaction with a methylene-active compound, is appropriately carried out at 50° to 80° C. It is advisable, in order to complete the reaction, to continue to stir the mixture for some time at these temperatures, 2 hours generally being sufficient.

The presence of a surface-active substance can have a favourable influence on the crystallisation or purity of the dyestuff produced. Preferably, non-ionic compounds, especially the oxethylation product of oleyl alcohol with approx. 20 mols of ethylene oxide, are employed.

On cooling, the resulting styryl dyestuff separates out in almost quantitative yield and can be isolated in a pure form by filtration.

The preparation of the Vilsmeier reagent and the reaction thereof with (IV) is carried out in the customary manner. The sequence of these reactions has no influence on the course of the reaction.

The decomposition of the excess Vilsmeier reagent is carried out in a manner which is in itself known, with compounds containing hydroxyl groups, such as water, low molecular aliphatic alcohols, low molecular carboxylic acids and simple amines; as examples there may be mentioned: methanol, ethanol, n- and i-propanol, n-, i- and t-butanol, and n- and i-pentanol; formic acid, acetic acid and lactic acid; ammonia, dimethylamine, diethylamine, n-butylamine, diethanolamine, morpholine, piperidine, and pyridine, and many others, as well as mixtures thereof.

However, the use of aliphatic alcohols, especially methanol and ethanol is particularly advantageous.

The requisite amount of compounds containing OH groups, or of amines, for the decomposition of the unconverted Vilsmeier reagent varies from case to case and can therefore not be calculated exactly beforehand. In carrying out this procedure in practice, an appropriate method is therefore cautiously (because of the exothermic reaction!) to introduce dropwise such an amount of the compound containing OH groups or of the amine into the reaction vessel that the exothermic reaction has subsided and the reaction medium is easily stirrable.

In general, 0.5 to 5.0 equivalents of the particular compound used for the decomposition (for example methanol), relative to the acid halide (for example phosphorus oxychloride) required for the synthesis of the Vilsmeier complex, suffices for this purpose.

The preferred pH range for the condensation with methylene-active compounds (III) is between 6.5 and 9.

Suitable bases for adjusting the pH to this range are inorganic bases such as NaOH, KOH, NaHCO$_3$, Na$_2$CO$_3$, K$_2$CO$_3$, CH$_3$COONa, MgO or ammonia and organic bases, such as pyridine, piperidine, quinoline, triethylamine, trimethylamine, dimethylamine, diethanolamine, hexahydrodimethylaniline and others, as well as mixtures thereof. The organic bases can also be employed in the form of their salts, preferably acetates.

Possible starting materials for the reaction according to the invention are preferably those amines (IV) which correspond to the formula (IVa)

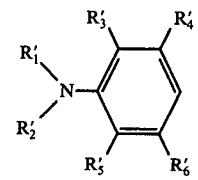

(IVa)

wherein
R'$_1$ denotes a straight-chain, branched, cyclic, saturated or unsaturated C$_1$-C$_6$-alkyl radical which can carry further substituents such as, for example, aryl, alkoxy, alkylmercapto, aryloxy, arylmercapto, heterylmercapto, alkylcarbonyloxy, arylcarbonyloxy, alkoxycarbonyloxy, alkylaminocarbonyloxy, arylaminocarbonyloxy, alkoxycarbonyl, alkylsulphonyl, arylsulphonyl, halogen, nitrile or the radical

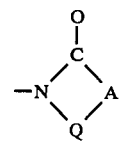

wherein
Q denotes CO, SO$_2$ or CH$_2$ and
A denotes ortho-arylene or C$_2$-C$_3$-alkylene,
or in which
R'$_1$ denotes the radical

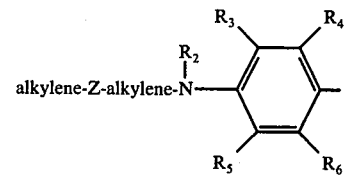

alkylene-Z-alkylene-N— wherein
Z denotes a direct bond or a bridge member such as O, S, SO, SO$_2$, NR, —O—CO—O—, $$-O-\overset{O}{\underset{\|}{C}}\text{-alkylene-}\overset{O}{\underset{\|}{C}}-O-,$$

$$-\underset{Z_1}{\overset{|}{N}}-CO\text{-alkylene-}CO-\underset{Z_1}{\overset{|}{N}}- \quad (Z_1 = H \text{ or alkyl}),$$

$$-O-\overset{O}{\underset{\|}{C}}-NH\text{-alkylene-}NH-\overset{O}{\underset{\|}{C}}-O,$$

—O-arylene-O—, —CO—O-alkylene-O—CO— or
—OCONH-arylene—NHCOO—
or wherein
R'$_1$ denotes an optionally substituted phenyl radical,
R'$_2$ denotes hydrogen or R'$_1$ and
R'$_3$ – R'$_6$ denote hydrogen, C$_1$-C$_4$-alkyl, C$_1$-C$_4$-alkoxy, nitro, bromine or chlorine
and wherein
R'$_1$ together with R'$_3$ or R'$_5$ conjointly form the remaining members of a non-aromatic 5-membered or 6-membered ring system which optionally contains oxygen or sulphur.

By the alkyl and alkoxy radicals mentioned above in any context (that is to say, for example, also alkylsulphonyl radicals), there are preferably to be understood radicals which possess 1 to 5 C atoms.

The aryl and aryloxy radicals mentioned in any context are preferably optionally substituted phenyl or phenoxy radicals.

Suitable heteryl radicals mentioned in any context are, for example, furane, thiophene, pyridine, pyrimidine, benzoxazole, benzthiazole and benzimidazole radicals, which can optionally contain further non-ionic substituents, such as $C_1$-$C_3$-alkyl, $C_1$-$C_3$-alkoxy, halogen, nitrile, $C_2$-$C_5$-carbalkoxy and phenyl.

The abovementioned alkylene radicals preferably contain 1 to 6 C atoms and can be straight-chain or branched, whilst by "ortho-arylene" there are preferably to be understood optionally substituted ortho-phenylene radicals.

The optionally substituted phenyl, phenylene or phenoxy radicals preferably carry the following substituents: $C_1$-$C_3$-alkyl, $C_1$-$C_3$-alkoxy, $C_2$-$C_5$-alkoxycarbonyl, halogen, nitro, nitrile and phenoxy.

The amines (IV) are known from the following patent literature, or obtainable according to the methods indicated therein: U.S. Pat. Nos. 2,226,054, 2,583,551, 2,583,614, 2,849,447, 2,850,520, 2,936,319, 3,247,211, 3,260,737, 3,326,960, 3,349,098, 3,390,168, 3,422,133, 3,453,270, 3,453,280, 3,483,218, 3,555,016, 3,597,434, 3,631,049, 3,635,957 and 2,909,561, and British Pat. Nos. 1,110,714, 1,124,866, 1,138,582, 1,147,125, 1,212,204 and 1,049,315, as well as Belgian Pat. Nos. 771,797 and 773,313.

Suitable methylene-active compounds (III) are preferably those of the formula

wherein
X' represents a nitrile group or one of the following acyl radicals: alkylcarbonyl, arylcarbonyl, alkoxycarbonyl, heterylcarbonyl, aryloxycarbonyl, alkylsulphonyl, arylsulphonyl, carbamoyl, aralkoxycarbonyl, N-alkylcarbamoyl and N,N-dialkylcarbamoyl.

By "alkyl" or "alkoxy"—mentioned in any context—there are to be understood alkyl or alkoxy radicals which possess 1 to 4 C atoms and can be substituted by OH, F, Cl, Br, CN, $C_1$-$C_3$-alkoxy or $C_2$-$C_4$-alkylcarbonyloxy, whilst by "aryl" or "aryloxy" there are preferably to be understood phenyl or phenoxy radicals which can be substituted by Cl, F, Br, $C_1$-$C_4$-alkoxy, $NO_2$, CN, $C_1$-$C_4$-alkyl, phenoxy or others.

Suitable aralkoxycarbonyl radicals are phenyl-$C_1$-$C_4$-alkoxycarbonyl radicals.

The definition given earlier applies to the term "heteryl".

The following methylene-active compounds may be mentioned by way of examples: malonic acid dinitrile, cyanoacetic acid methyl ester, cyanoacetic acid ethyl ester, cyanoacetic acid n-propyl ester, cyanoacetic acid n-butyl ester, cyanoacetic acid n-amyl ester, benzoylacetonitrile, 4-chlorobenzoylacetonitrile, 4-toluylacetonitrile, 2-phenylacetonitrile, 2-furoylacetonitrile, methylsulphonylacetonitrile, ethylsulphonylacetonitrile, phenylsulphonylacetonitrile, 4-tolylsulphonylacetonitrile, benzylsulphonylacetonitrile, cyanoacetamide, cyanoacetmethylamide, cyanoacetdimethylamide, cyanoacetdiethylamide, cyanoacetic acid phenylethyl ester, benzyl ester and phenylpropyl ester.

In addition, the methylene-active compounds mentioned in the patent literature cited earlier can be used.

The process according to the invention will be explained in more detail with the aid of the following characteristic illustrative embodiments: herein, the parts mentioned are parts by weight, unless otherwise stated. The yields indicated relate to amine (IV) employed, and if no quantity for this is stated, the calculation was made relative to the precursor for which the quantity is stated. The temperatures mentioned are degrees Centigrade. The word "emulsifier" represents the reaction product of oleyl alcohol with approx. 20 mols of ethylene oxide.

EXAMPLE 1

39.5 Parts of N-chloroethyl-N-ethyl-m-toluidine in 49 parts of dimethylformamide are reacted with 45 parts of the K salt of 4-carbomethoxybenzoic acid, by heating for 4 hours to 130°–140°, to give N-ethyl-N-β-(4'-carbomethoxybenzoyloxy)-ethyl-m-toluidine. The batch is then cooled to 50° and 34 parts of phosphorus oxychloride are added over the course of ½ hour at 50°–60°. The melt is stirred for approx. 15 hours longer at 60°–65°. It is then cooled to 40°–45° and 120 parts of methanol are added dropwise to the mixture over the course of ½ hour at 40°–50°. The pH is then adjusted to a value of approx. 8 by adding approx. 50 parts of concentrated ammonia. 13.8 Parts of malonic acid dinitrile are then added to the mixture and the whole is postcondensed for a further 2 hours at 50°–60°, in the course of which the dyestuff separates out as crystals. After cooling to room temperature, the dyestuff which has separated out, of the formula

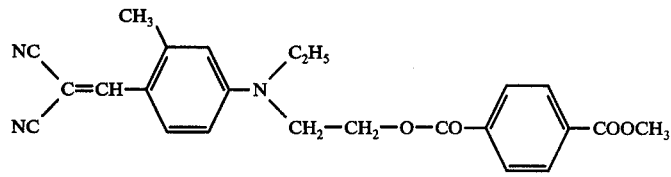

is filtered off and rinsed with 120 parts of methanol. 71 parts (85% of theory) of a dyestuff which dyes polyester fibres and polyamide fibres as well as triacetate rayon in clear greenish-tinged yellow shades of very good fastness to light, wet processing and sublimation are obtained.

EXAMPLE 2

42.3 Parts of N-butyl-N-chloroethyleniline are mixed with 49 parts of dimethylformamide and 45 parts of the K salt of 4-carbomethoxybenzoic acid and the mixture is heated to 130°–140° for 5 hours. 34 Parts of phosphorus oxychloride are now added to the N-butyl-N-β(4'-carbomethoxybenzoyloxy)ethylaniline which is formed in practically quantitative yield, without intermediate isolation, over the course of ½ hour at 50°–60°, and the whole is stirred for a further 10–15 hours at this temperature. The melt is then allowed to run into 120 parts of ethanol at room temperature. The pH value is adjusted to approx. 5 by adding approx. 40 parts of 50% strength sodium hydroxide solution. 24.5 Parts of cyanoacetic acid ethyl ester are then added and the mixture is boiled for 2 hours under reflux. On cooling, the styryl dyestuff of the formula

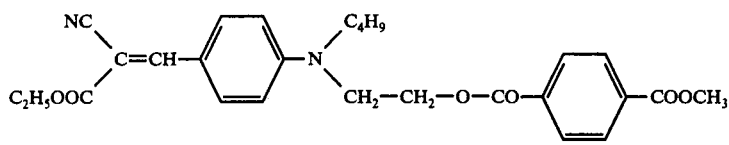

crystallises out in almost quantitative yield. It is filtered off and washed with 150 parts of ethanol. 85 Parts (89% of theory) of a yellow dyestuff of melting point 119°–121° are obtained. Similarly good results are obtained if, using appropriate starting materials and working under the reaction conditions mentioned in the above examples, the dyestuffs described in British patent specifications Nos. 1,027,026 and 1,049,315 are prepared.

EXAMPLE 3

A mixture of 39.5 parts of N-chloroethyl-N-ethyl-m-toluidine and 52 parts of dimethylformamide is heated with 40.5 parts of the K salt of 4-methoxybenzoic acid for 4 hours to 130°–140°. After cooling to 50°, 35 parts of phosphorus oxychloride are added dropwise to the mixture. The melt is stirred for a further 10–15 hours at 70°–80° and cooled to 40°, and 140 parts of isopropanol are added slowly. The pH value of the mixture is then adjusted to approx. 8 with 11 parts of piperidine and 48 parts of concentrated ammonia and 14 parts of malonic acid dinitrile are then added. The mixture is stirred for some hours longer at 60°–65° and is cooled to room temperature, whereupon the styryl dyestuff of the formula

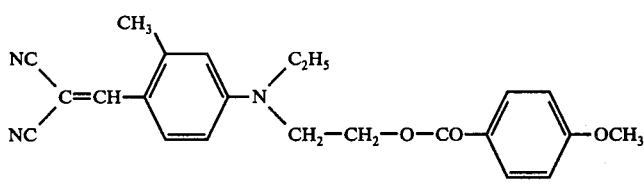

separates out in yellow crystals. The dyestuff is filtered off and washed with 150 parts of methanol. 67.5 Parts (87% of theory) of a dyestuff of melting point 145°–148° are obtained.

Similarly good results are obtained if, using appropriate starting materials, under the conditions mentioned in the preceding Example 3, dyestuffs described in British patent specification No. 1,138,582 are prepared.

EXAMPLE 4

73.5 Parts of 2-mercapto-benzthiazole and 79.0 parts of N-ethyl-N-(β-chloroethyl)-m-toluidine are successively added to a solution of 10.15 parts of sodium in 200 parts of absolute ethanol and the mixture is heated to the refluxing temperature for 6 hours. After cooling, the mixture is poured into 1,000 parts of water, the pH is adjusted to 9–10 and the oil which has separated out is taken up in chloroform. The chloroform solution is washed with water in the usual manner, dried over calcium chloride and evaporated. 127.2 Parts of crude N-ethyl-N-(β-benzthiazolylmercaptoethyl)-m-toluidine are obtained as an oily residue. 65.6 Parts of this toluidine base are dissolved in 43.8 parts of dimethylformamide, 34 parts of phosphorus oxychloride are added dropwise over the course of about one hour at below 50°, and the mixture is stirred for a further 15 hours, at 60°–65°. It is then allowed to cool to approx. 40° and a total of 150 parts by volume of methanol is added—initially dropwise, and whilst cooling externally to 40°–50° until the exothermic reaction has subsided—7 parts of emulsifier are introduced and the pH value is now adjusted to 7–8 by dropwise addition of approx. 55 parts by volume of concentrated aqueous ammonia whilst cooling with water. A solution of 13.8 parts of malodinitrile in 15 parts of methanol is then added, the reaction mixture is stirred for 2 hours at 55°–60° and after cooling the dyestuff of the formula

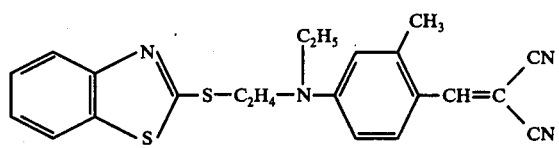

which has precipitated is filtered off. The product is washed with 150 parts by volume of methanol and then with 750 parts of warm water, and after drying at 70° in a vacuum drying cabinet 70.6 parts of dyestuff (87.5% of theory) of melting point 190°–192° are obtained.

EXAMPLE 5

27.5 Parts of N-ethyl-N-β-(4'-chlorophenylmercapto)ethyl-m-toluidine, prepared from N-ethyl-N-(β-chloroethyl)-m-toluidine and 4-chlorothiophenol analogously to Example 4, are reacted as the crude product—again as described in Example 4—with 19.7 parts of dimethylformamide and 15.3 parts of phosphorus oxychloride; after cooling to 40°, the mixture is decomposed with 68 parts by volume of methanol over the course of approx. 30 minutes at not more than 40°–50°, 3.15 parts of emulsifier are added and the pH is adjusted to 8 by dropwise addition of 25.5 parts by volume of aqueous concentrated ammonia. A solution of 6.28 parts of malodinitrile in 10 parts of methanol is then added, the mixture is stirred for 3 hours at 50°–55°, and after cooling the yellow dyestuff which has separated out is filtered off and washed with approx. 100 parts by volume of methanol and then with water. After drying in vacuo at 50°, the yield is 29.8 parts of dyestuff (86.9% of theory) of the structure

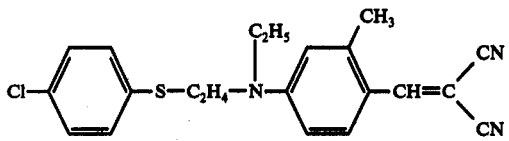

and of melting point 118°-120°.

Comparably excellent yields of the corresponding yellow dyestuffs are also obtained when using further mercapto compounds or thiophenols such as are employed in U.S. Pat. No. 3,635,957 and German Offenlegungsschrift (German Published Specification) No. 1,569,698, if the process according to the invention is carried out as described in Examples 4 and 5. It is not absolutely essential to work up the toluidine bases with water prior to their formylation; instead it suffices in general, when carrying out the process, first to free the bases as completely as possible of ethanol by applying a vacuum.

EXAMPLE 6

76.5 Parts of the isomer mixture from the reaction of styrene oxide with N-ethyl-m-toluidine are dissolved in 100 parts of dimethylformamide, 39.3 parts of phenylisocyanate are added and the mixture is warmed to 60°-65° for 3 hours. 60 Parts of phosphorus oxychloride are then added dropwise whilst cooling to below 50° and the mixture is stirred for a further 15 hours at 50°. The mixture is decomposed by running in 264 parts by volume of methanol (over the course of approx. 20 minutes; internal temperature at most 40°-50°), 10.5 parts of emulsifier are added, the pH is adjusted to 7.5-8 by addition of 99.4 parts by volume of concentrated aqueous ammonia (external cooling) and after addition of a solution of 20.7 parts of malodinitrile in 30 parts by volume of methanol the mixture is heated to approx. 70° for 3 hours. The dyestuff which has crystallised out is filtered off after cooling the mixture, and is washed with 250 parts by volume of methanol and subsequently well washed with warm water. After drying in vacuo at 50°, 96.8 parts of dyestuff (71.5% of theory) of melting point 164°-168° are obtained; this dyestuff is a mixture of the following isomers:

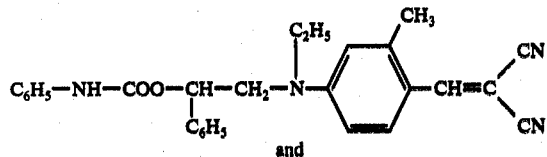

and

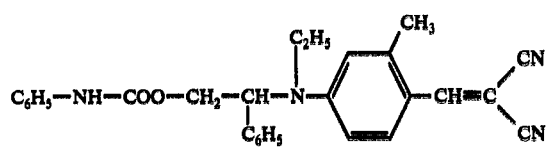

Similarly superior yields of dyestuffs are also obtained on applying the process according to the invention to further reaction products of styrene oxides with aniline bases, such as are employed for the manufacture of dyestuffs in German Offenlegungsschrift (German Published Specification) No. 2,147,811.

EXAMPLE 7

23.2 Parts of N-ethyl-N-β-(4'-phenylphenoxy)-ethyl-m-toluidine (melting point 90°-92°; prepared analogously to Example 4 from 4-hydroxybiphenyl) are taken up in 30.6 parts of dimethylformamide and reacted, in the manner described above, with 13 parts of phosphorus oxychloride for 15 hours at 50°, and the mixture is subsequently decomposed by dropwise addition of 60 parts by volume of methanol. 3.5 Parts of emulsifier are added, the pH is adjusted to 7.5-8 in the usual manner with approx. 22 parts by volume of concentrated aqueous ammonia, 4.85 parts of malodinitrile dissolved in 10 parts by volume of methanol, are added, and the reaction to give the styryl dyestuff is effected by stirring for three hours at 70°. After the customary working-up of the product which has precipitated as a powder, 25.4 parts of dyestuff (89.0% of theory) of melting point 125°-127° and of the structure

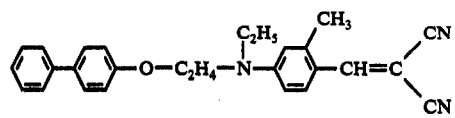

are obtained. The process according to the invention also permits the manufacture of further dyestuffs of British patent specification No. 1,110,714, in similarly excellent yields, with circumvention of the intermediate isolation of the corresponding aldehydes.

EXAMPLE 8

17.0 Parts of β,β'-bis-(3-methyl-N-ethyl-anilino)-diethyl ether are dissolved in 21.9 parts of dimethylformamide and reacted with 18.4 parts of phosphorus oxychloride in the usual manner for 15 hours at 50°. 81 Parts by volume of methanol are then added whilst cooling, 3.5 parts of emulsifier are introduced, the pH is adjusted to 7.5-8 with approx. 31 parts by volume of concentrated aqueous ammonia and finally a solution of 6.9 parts of malodinitrile in 10 parts by volume of methanol is added and the reaction mixture is stirred for 3 hours at 70°. The dyestuff crystallises out even whilst the mixture is hot and, after cooling the mixture, is filtered off, washed in the usual manner with methanol and water, and dried in vacuo at 50°. Yield 22.0 parts (89.4% of theory) of a brownish-yellow crystal powder of melting point 161°-164.5° and of the formula

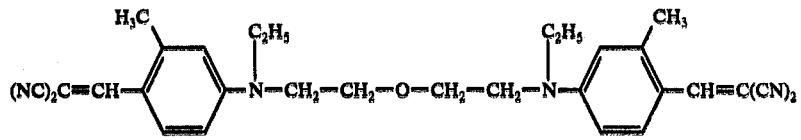

Very good yields of dyestuffs are also obtained on reacting other aniline bases of Swiss Pat. Nos. 492,758 and 516,628 by the process of the invention analogously to the preceding example. This is further evidenced by the following example.

EXAMPLE 9

46.8 Parts of the adipic acid ester of N-ethyl-N-(β-hydroxyethyl)-m-toluidine of melting point 72°–73° are stirred into 44 parts of dimethylformamide and reacted with 36.8 parts of phosphorus oxychloride, in the manner fully described initially, by stirring for 15 hours at 50°. To decompose the mixture, 162 parts by volume of methanol are allowed to run in whilst cooling, 7 parts of emulsifier are added and the pH is adjusted to 7.5–8 with approx. 62 parts by volume of concentrated aqueous ammonia. After adding 13.8 parts of malodinitrile dissolved in 20 parts by volume of methanol, the mixture is allowed to react for 2 hours at 70°. After it has cooled, the yellow dyestuff which has precipitated is filtered off and washed and dried in the usual manner. Yield: 53.9 parts (87.0% of theory) of the dyestuff of the structure

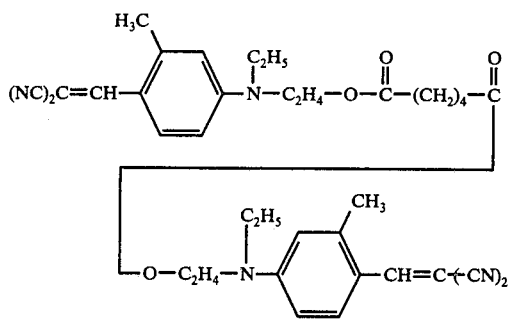

of melting point 123°–128°.

EXAMPLE 10

28.3 Parts of N-ethyl-N-β-(phenylcarbamoyloxy)-ethyl-m-toluidine (of melting point 93°–95°) are dissolved in 45 parts of dimethylformamide and reacted in the usual manner with 18.4 parts of phosphorus oxychloride for 15 hours at 50°. After methanolysis by addition of 81 parts by volume of methanol, 3.5 parts of emulsifier are added and the pH of the mixture is adjusted to 7.5–8 by means of approx. 31 parts by volume of concentrated aqueous ammonia, whilst cooling. A solution of 6.7 parts of malodinitrile in 10 parts by volume of methanol is then added, the mixture is stirred for 3 hours at 70°, and the dyestuff is separated out in a crystalline form by allowing 200 parts of 50% strength aqueous methanol to run in. After working up in the usual manner, the yield is 31.1 parts of dyestuff (87.3% of theory), of melting point 141°–142° and of the formula

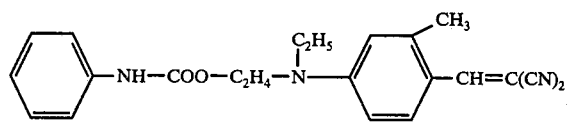

The remaining dyestuffs of German Auslegeschrift (German Published Specification) No. 1,067,156 and of Japanese Pat. No. 70/28,026 can also be prepared with similarly excellent yields by the process of the invention.

EXAMPLE 11

24.1 Parts of N-benzyl-N-β-hydroxyethyl-m-toluidine are dissolved in 32.0 parts of dimethylformamide, 13.1 parts of phenylisocyanate are added and complete urethane formation is achieved by warming the mixture for three hours to 60°–65°. 20.0 parts of phosphorus oxychloride are now added dropwise in the usual manner and the mixture is stirred for 15 hours at 50°–55°. After decomposing the Vilsmeier mixture with 81 parts by volume of methanol, 3.5 parts of emulsifier are added, and the pH value is adjusted to 7.5–8 by dropwise addition of approx. 31 parts by volume of concentrated aqueous ammonia. 6.9 Parts of malodinitrile dissolved in 10 parts by volume of methanol are now added to the mixture, which is stirred for 3 hours at 70°. In the course thereof, the dyestuff of the formula

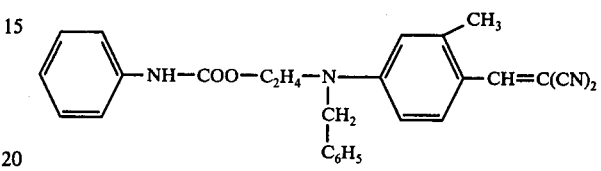

precipitates in orange crystals and is isolated in the usual manner. It melts at 143°–144° and its yield is 34.9 parts (80.1% of theory).

The other dyestuffs of German Offenlegungsschriften (German Published Specifications) Nos. 2,042,498 and 2,147,810 also become obtainable in very good yields by the process according to the invention analogously to the example described.

EXAMPLE 12

26.9 Parts of N-(β-phenylpropyl)-N-(β-hydroxyethyl)-m-toluidine in 22.0 parts of dimethylformamide are reacted—analogously to Example 11—with 13.1 parts of phenylisocyanate, the Vilsmeier formylation is carried out immediately afterwards by addition of 20.0 parts of phosphorus oxychloride, and thereafter the procedure described in Example 11 is followed, except that the dyestuff is precipitated as a resin by addition of 250 parts of water, separated off, washed with water and dried in vacuo at 50°. 45 Parts of the yellow dyestuff (97% of theory) of the formula

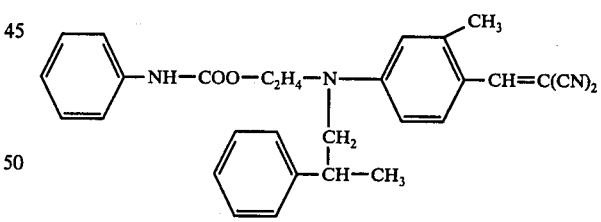

are obtained in the form of a brittle, brown-yellow resin.

Further examples from German Offenlegungsschrift (German Published Specification) No. 2,058,405 can be prepared in the same manner by the process according to the invention, again in excellent yields.

EXAMPLE 13

20.5 Parts of 2,7-dimethyl-N-(β-hydroxyethyl)-1,2,3,4-tetrahydroquinoline are dissolved in 22.0 parts of dimethylformamide, after addition of 13.1 parts of phenylisocyanate the phenylmethane formation is completed by warming to 60°–65° for 3 hours, and the Vilsmeier formylation is then carried out in the usual manner by dropwise addition of 20 parts of phosphorus oxychloride and stirring for a further 15 hours at approx. 50°. The mixture is decomposed with 81 parts by volume of methanol as described in the preceding examples and after introducing 3.5 parts of emulsifier, adjusting the pH value to 7.5-8 by dropwise addition of approx. 31 parts by volume of concentrated aqueous ammonia and addition of 6.9 parts of malodinitrile in 10 parts by volume of methanol, the reaction to give the dyestuff is effected by stirring for 3 hours at 70°. The product is first obtained as an oil but crystallises throughout on prolonged stirring. The usual working up gives 35.4 parts (88.5% of theory) of the dyestuff of the structure

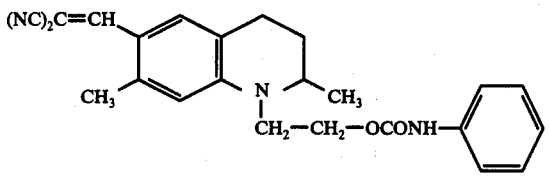

of melting point 120°-122°.

EXAMPLE 14

23.3 Parts of 2,2,4,7-tetramethyl-N-(β-hydroxyethyl)-1,2,3,4-tetrahydroquinoline in 55 parts of dimethylformamide are reacted analogously to Example 13 with 13.1 parts of phenylisocyanate for 3.5 hours at 60°-65°, 20.0 parts of phosphorus oxychloride are now added to the mixture and the whole is stirred for 15 hours at 50°. 81 Parts by volume of methanol are then added in accordance with the invention, 3.5 parts of emulsifier are introduced into the mixture, followed by approx. 31 parts by volume of concentrated aqueous ammonia until the pH is 7.5-8, and subsequently by a solution of 6.9 parts of malodinitrile in 10 parts by volume of methanol. During the 3 hours' reaction at 70°, the yellow dyestuff precipitates and is isolated as described in the preceding examples. 36.4 parts of the product (85.1% of theory) of the formula

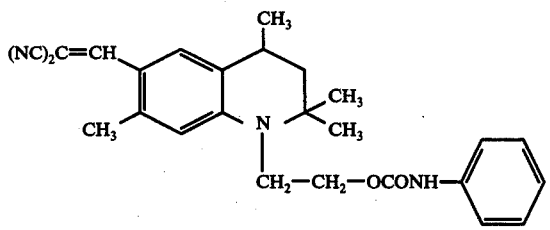

of melting point 171°-174° are obtained.

The remaining dyestuffs of German Auslegeschrift (German Published Specification) No. 1,292,280 and the dyestuffs of U.S. Pat. Nos. 3,597,434 and 3,631,049 can be prepared in outstanding yields in accordance with the process described here, similarly to the dyestuffs of Examples 13 and 14.

Entirely analogously, and with no less excellent results, the process according to the invention also gives the related styryl dyestuffs of the 1,2,3,4-tetrahydrobenzo(b)-1,4-oxazine type which are described in U.S. Pat. No. 3,453,270, and of the 2,3-dihydroindole type, known from German Offenlegungsschrift (German Published Specification) No. 1,959,706.

EXAMPLE 15

30 Parts of phosphorus oxychloride are added dropwise at below 50° to a solution of 28.2 parts of N-ethyl-N-(β-benzamidoethyl)-m-toluidine in 40 parts of dimethylformamide and the reaction is allowed to go to completion by stirring for a further 15 hours at 50°. After cooling, 90 parts by volume of methanol are added to the mixture in the usual manner, 3.5 parts of emulsifier are introduced and the pH value is adjusted to 7.5-8 by dropwise addition of approx. 55 parts by volume of concentrated aqueous ammonia. After addition of 6.9 parts of malodinitrile dissolved in 10 parts by volume of methanol, the mixture is warmed to 70° for 3 hours. In the course thereof, the dyestuff crystallises out and is filtered off, after the mixture has cooled, and washed and dried in the usual manner. The yield is 30.8 parts (86.0% of theory) of the dyestuff of the structure

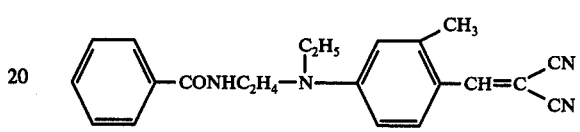

of melting point 166°-167°.

The process according to the invention also gives the further dyestuffs of this type, described in British patent specification No. 1,263,257, in similarly good yields.

EXAMPLE 16

34.0 Parts of sodium benzoate monohydrate are introduced, whilst stirring, into a solution of 23.2 parts of N,N-bis-(β-chloroethyl)-m-toluidine in 100 parts of dimethylformamide, and the mixture is brought to 135°-140° over the course of 30 minutes and stirred for a further 5 hours at this temperature. After cooling to 30°-40°, 27.6 parts of phosphorus oxychloride are added dropwise at below 50° and the reaction is allowed to go to completion by stirring for a further 15 hours at 50°. The Vilsmeier mixture is then decomposed in the manner according to the invention by dropwise addition of 85 parts by volume of methanol, 3.5 parts of emulsifier are added and the pH of the mixture is adjusted to 7.5-8 by means of 46 parts by volume of concentrated aqueous ammonia, in each case avoiding the temperature rising to substantially above 50°. After addition of 6.9 parts of malodinitrile dissolved in 10 parts by volume of methanol, the reaction mixture is warmed for 3 hours to 70°, in the course of which the dyestuff separates out as crystals. After cooling the mixture, the dyestuff is filtered off, washed twice with 50 parts by volume of methanol and then with a total of 1,000 parts of water and dried in vacuo at 50°. 43.6 parts (91.0% of theory) of orange dyestuff powder of melting point 148°-149°, having the structure

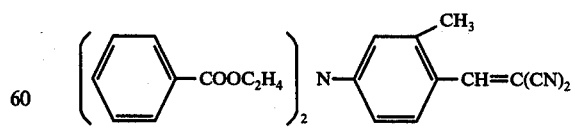

are obtained.

The remaining styryl dyestuffs mentioned in German Offenlegungsschrift (German Published Specification) No. 2,114,574 and those of Belgian Pat. No. 660,762 and U.S. Pat. Nos. 2,583,551 and 2,583,614 also become accessible by the process according to the invention, in the same simple manner and with similarly excellent yields.

EXAMPLE 17

28.5 Parts of 94.6% strength N-ethyl-N-(β-hydroxy-γ-phenoxypropyl)-m-toluidine are taken up in 22.0 parts of dimethylformamide and converted to the phenylurethane by adding 13.0 parts of phenylisocyanate and heating for 3 hours to 60°-65°. 20 Parts of phosphorus oxychloride are then added dropwise to the mixture at below 50° and the reaction is completed by stirring for a further 15 hours at 50°. 80 Parts by volume of methanol are subsequently added in the manner according to the invention (with cooling), 3.5 parts of emulsifier are introduced and the pH is adjusted to a weakly basic value of 7.5-8 by dropwise addition of 31 parts by volume of concentrated aqueous ammonia. A solution of 6.9 parts of malodinitrile in 10 parts by volume of methanol is now added and the condensation to the dyestuff of the formula

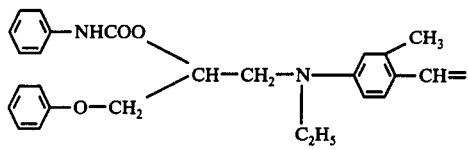

is effected over the course of 3 hours at 70°. The dyestuff, which in the first place forms as an oil, crystallises throughout after prolonged stirring and is isolated, washed and dried, in the usual manner. The yield is 39.5 parts of reddish-yellow crystals (87.0% of theory), of melting point 148°-151°.

Other dyestuffs of the same type, such as are described in Japanese Pat. Nos. 28,026/70 and 29,466/71, can also be prepared analogously in excellent yields by the process according to the invention.

EXAMPLE 18

35.8 Parts of N-ethyl-N-(β-hydroxyethyl)-3-aminotoluene are added dropwise over the course of approx. 40 minutes to 61.2 parts of phosphorus oxychloride at 80°, whilst stirring, the mixture is stirred for a further hour at 80° and after cooling to 50° 44 parts of dimethylformamide are allowed to run in in such a way that the temperature does not exceed 60°. The mixture is then stirred for a further 15 hours at 50° and decomposed with 162 parts by volume of methanol, 7 parts of emulsifier are added and the reaction mixture is neutralised over the course of approx. 30 minutes by dropwise addition of 85 parts by volume of aqueous concentrated ammonia. After adding a solution of 13.8 parts of malodinitrile in 20 parts by volume of methanol, the mixture is stirred for 3 hours at 60°-70° and after cooling the dyestuff which has crystallised out is filtered off. After the customary washing of the product with methanol and then with a copious amount of water, the yellow dyestuff is dried in vacuo at 50°. 47.5 parts (86.8% of theory) of dyestuff of the formula

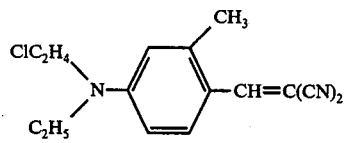

of melting point 131°-133° are obtained.

Entirely analogously, any other N-chloroalkyl- and N,N-bis-(chloroalkyl)-dyestuffs are obtained in excellent yields from the corresponding hydroxyalkylamine bases. These dyestuffs are of particular importance in that they can be employed as intermediate products for the preparation of other valuable styryl dyestuffs.

We claim:

1. Process for the preparation of a styryl dyestuff free of ionogenic groups of the formula

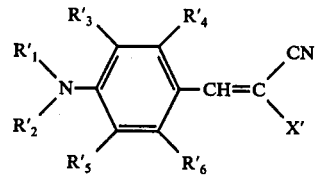

wherein

R'₁ is a straight-chain, branched, cyclic, saturated or unsaturated C₁-C₆-alkyl radical which is unsubstituted or which is substituted with a member selected from the group consisting of phenyl, substituted phenyl, C₁-C₅-alkoxy; C₁-C₅-alkylmercapto, phenyloxy, substituted phenyloxy, phenylmercapto, substituted phenylmercapto, heterylmercapto, (C₁-C₅-alkyl)-carbonyl-oxy, phenylcarbonyloxy, substituted phenylcarboxyloxy, (C₁-C₅)-alkoxy-carbonyloxy, (C₁-C₅-alkylamino)-carbonyloxy, phenylaminocarbonyloxy, substituted phenylaminocarbonyloxy, (C₁-C₅-alkoxy)-carbonyl, C₁-C₅-alkyl sulphonyl, phenyl sulphonyl, substituted phenylsulphonyl, halogen, —CN, or

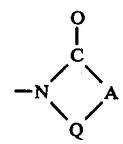

in which

Q is CO, SO₂ or CH₂;

A is ortho-arylene or C₂-C₃-alkylene; or R'₁ is

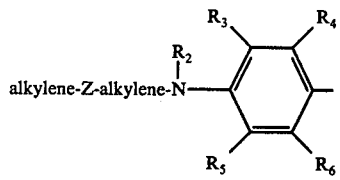

in which

Z is a direct bond,

O, S, SO, SO₂, NR, —O—CO—O—,

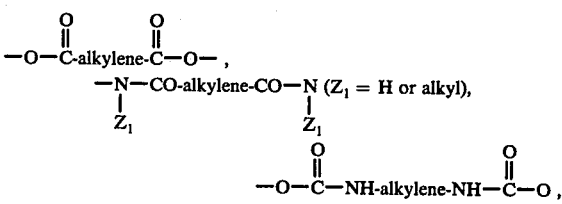

—O—arylene—O—, —CO—O—alkylene—O—CO— or —OCONH-arylene-NHCOO—; phenyl or substituted phenyl;

$R'_2$ is hydrogen or $R'_1$;

$R'_3$–$R'_6$ are hydrogen, $C_1$–$C_4$-alkyl, $C_1$–$C_4$-alkoxy, nitro, bromine or chlorine; or $R'_1$ together with $R'_3$ or $R'_5$ conjointly form the remaining members of a non-aromatic 5-membered or 6-membered ring system which optionally contains oxygen or sulphur;

said heteryl is selected from the group consisting of furane, thiophene, pyridine, pyrimidine, benzoxazole, benzthiazole, benzimidazole and the foregoing heterocyclic radicals substituted with $C_1$–$C_3$-alkyl, $C_1$–$C_3$-alkoxy, halogen, nitrile, $C_2$–$C_5$-carbalkoxy or phenyl, said alkylene radicals are $C_1$–$C_6$-alkylene; and said arylene radicals are phenylene or phenylene substituted by $C_1$–$C_3$-alkyl, $C_1$–$C_3$-alkoxy, $C_2$–$C_5$-alkoxycarbonyl, halogen, nitro, —CN or phenoxy; said substituted phenyl is substituted with $C_1$–$C_3$-alkyl, $C_1$–$C_3$-alkoxy, $C_2$–$C_5$-alkoxycarbonyl, halogen, nitro, nitrile or phenoxy;

X' is CN, ($C_1$–$C_4$-alkyl)-carbonyl, substituted ($C_1$–$C_4$-alkyl)-carbonyl, ($C_1$–$C_4$-alkoxy)-carbonyl, substituted ($C_1$–$C_4$-alkoxy)-carbonyl, heterylcarbonyl, phenoxycarbonyl, substituted phenoxycarbonyl, $C_1$–$C_4$-alkyl-sulphonyl, substituted $C_1$–$C_4$-alkylsulphonyl, carbamoyl, phenyl-($C_1$–$C_4$-alkoxy)-carbonyl, N-($C_1$–$C_4$-alkyl)-carbamoyl, substituted N-($C_1$–$C_4$-alkyl)-carbamoyl, N,N-di($C_1$–$C_4$-alkyl)-carbamoyl, or substituted N,N-di($C_1$–$C_4$-alkyl)-carbamoyl;

wherein in X' said substituted alkyl and alkoxy radicals are substituted by OH, F, Cl, Br, CN, $C_1$–$C_3$-alkoxy or $C_2$–$C_4$-alkylcarbonyloxy, and said substituted phenyl or phenoxy radicals are substituted by Cl, F, Br, $C_1$–$C_4$-alkoxy, $NO_2$, CN, $C_1$–$C_4$-alkyl, or phenoxy, and "heteryl" is defined as above;

comprising a one-pot reaction in which an amine of the formula

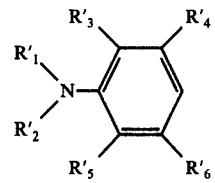

is treated with at least 1 equivalent of a Vilsmeier reagent;

unconverted Vilsmeier reagent is decomposed by the addition of aliphatic alcohol;

the pH value is adjusted to above 4 by addition of base; and the reaction product without any intermediate isolation is reacted with a methylene-active compound of the formula

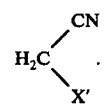

2. Process of claim 1, in which the pH-value is adjusted by addition of aqueous ammonia or NaOH.

3. Process of claim 1, in which a Vilsmeier reagent prepared from phosphorus oxychloride and dimethylformamide is used.

4. Process of claim 1 in which said aliphatic alcohol is methanol.

5. Process of claim 1 in which each of said radicals defined as unsubstituted or substituted is unsubstituted.

6. Process of claim 1 for preparing a styryl dyestuff free of ionogenic groups of the formula

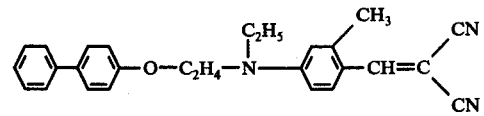

in which said amine has the formula

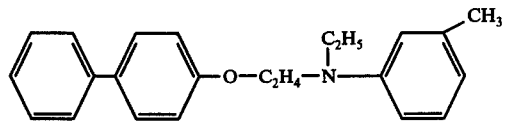

said Vilsmeir reagent is the reaction product of dimethylformamide and phosphorus oxychloride and said methylene active compound is malodinitrile.

* * * * *